Figure 1:
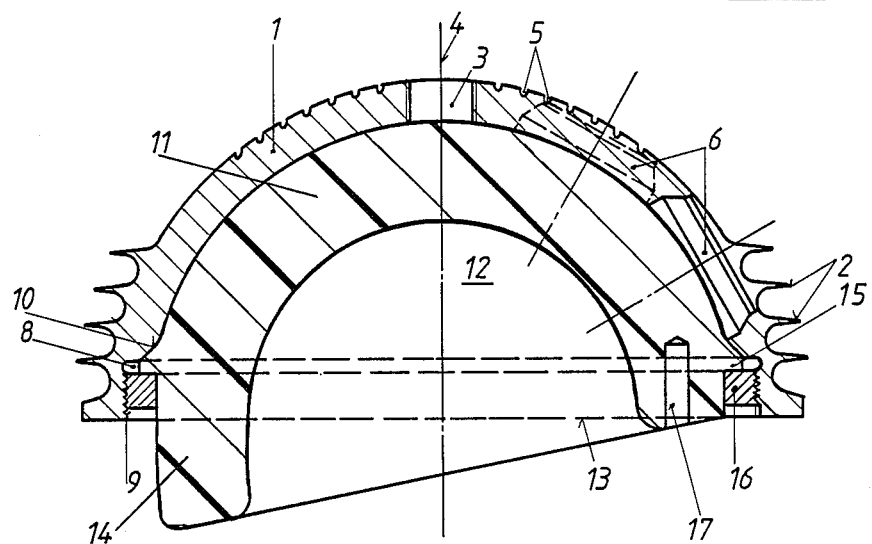

United States Patent [19]

Wagner

[11] Patent Number: 4,871,368
[45] Date of Patent: Oct. 3, 1989

[54] ARTIFICAL ACETABULUM

[75] Inventor: Heinz Wagner, Schwarzenbruck, Fed. Rep. of Germany

[73] Assignees: Sulzer Brothers Limited, Winterthur; Protek AG, Berne, both of Switzerland

[21] Appl. No.: 174,107

[22] Filed: Mar. 28, 1988

[30] Foreign Application Priority Data

Mar. 30, 1987 [CH] Switzerland ............ 1219/87

[51] Int. Cl.$^4$ .............................. A61F 2/32; A61F 2/30
[52] U.S. Cl. .............................. 623/22; 623/18
[58] Field of Search ............ 623/22, 18, 19, 20, 623/21, 23; 403/135, 132, 133

[56] References Cited

U.S. PATENT DOCUMENTS

| 3,574,368 | 4/1971 | Songer | 403/135 |
| 3,740,769 | 6/1973 | Haboush | 623/22 |
| 4,650,491 | 3/1987 | Parchinski | 623/22 |
| 4,690,581 | 9/1987 | Umemoto et al. | 403/133 |
| 4,795,469 | 1/1989 | Oh | 623/22 |
| 4,795,470 | 1/1989 | Goymann et al. | 623/18 |

FOREIGN PATENT DOCUMENTS

| 2319098 | 11/1973 | Fed. Rep. of Germany | 623/22 |
| 321761 | 11/1929 | United Kingdom | 403/135 |
| 1371335 | 10/1974 | United Kingdom | 623/22 |

OTHER PUBLICATIONS

Engh, C. A. et al., "Mecring TM", Cenuntless Acetabulum System, pp. 6-11, 10-85.

Primary Examiner—Richard J. Apley
Assistant Examiner—Stephanie L. Iantorno
Attorney, Agent, or Firm—Kenyon & Kenyon

[57] ABSTRACT

The artifical acetabulum is formed of an outer metal shell having an annular shoulder, an acetabular body having an annular flange seated on the shoulder and a threaded ring threaded into the shell in order to clamp the flange of the acetabular body against the shoulder of the shell. The acetabular body is constructed in an asymmetric manner with an extension to prevent dislocations of a joint head and can be rotated into precise position before tightening of the threaded ring in place.

8 Claims, 1 Drawing Sheet

ARTIFICAL ACETABULUM

This invention relates to an artificial acetabulum. More particularly this invention relates to an artificial acetabulum for a hip joint implant.

As is known, various types of artificial acetabulums have been used in hip implant procedures. For example, French Patent 2,210,909 describes an artificial acetabulum consisting of an outer metal shell and a plastic acetabular body containing an acetabular shell for receiving a joint head which can be secured in the metal shell by means of an annular flange of the acetabular body being mounted on an offset within the outer shell In order to connect the artificial acetabulum to the metal shell, the artificial acetabulum is threaded into the shell For this purpose, both the body and shell are provided in the equatorial regions with appropriate threads. However, since threads can be more or less strongly "tightened", it has not been possible to exactly achieve a particular position for the artificial acetabulum body upon implantation, for example, in the case of artificial acetabulum bodies which are not formed in a symmetric manner and which require installation in a particular position relative, for example, to the frontal plane of the human body.

Accordingly, it is an object of the invention to provide an artificial acetabulum in which an acetabular body can be rotated within an outer metal shell into a precise position.

It is another object of the invention to provide an artificial acetabulum in which an asymmetric acetabulum body can be precisely positioned in an artificial hip joint.

Briefly, the invention provides an artificial acetabulum comprising an outer metal shell having an annular shoulder, a synthetic acetabulum body mounted in the shell with a socket for receiving a spherical joint head and an annular flange seated on the shoulder of the shell and a ring mounted in the metal shell in secured relation to clamp the flange of the acetabulum body against the shoulder of the metal shell.

Since the securement of the acetabulum body in the outer shell takes place solely by clamping the annular flange, the acetabulum body may be rotated in any given direction before being clamped into the outer shell. Hence, in acetabula in which the outer shell is axially symmetrical to a polar axis while the acetabular body is shaped asymmetrically, the asymmetry of the acetabular body can be fixed exactly in any given "geographical longitude".

The outer metal shell may be provided with threads on the outer surface in order to be screwed into a pelvic bone. In addition, the shell may be provided with bone screws to provide for additional fixation. In order to offer a number of options to the surgeon for "setting" these screws, the outer shell may be equipped with at least two rows of bores distributed in the circumferential direction for the penetration of the bone screws. In general, at least isolated ones of these bores, for example, two or three, are "utilized" in the practical case. Bone tissue may then be allowed to grow into the other bores in the course of time.

Advantageously, the material for the outer shell may be selected from a metal or metal alloy customarily used in implantation technology. For example, use may be made of pure titanium or a titanium alloy. Likewise, the clamping ring may also be made of the same or similar metals. A preferred synthetic material for the acetabular body is polyethylene of a quality and specification customary for implants of this nature.

Figure 2:
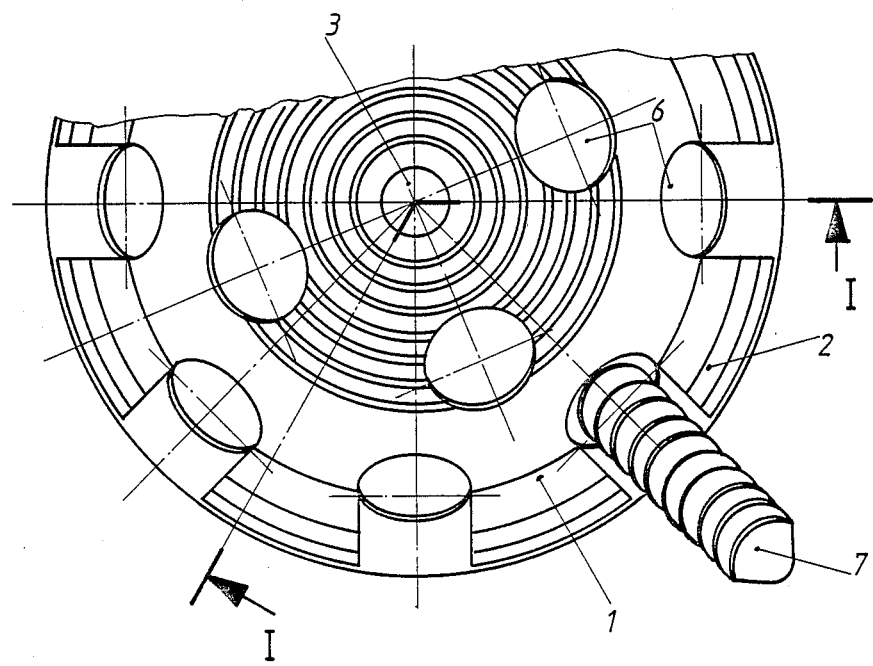

These and other objects and advantages of the invention will become more apparent from the following detailed description taken in conjunction with the accompanying drawings wherein:

FIG. 1 illustrates a cross sectional view taken on line I—I of FIG. 2 of an acetabulum constructed in accordance with the invention; and FIG. 2 illustrates a partial plan view of the acetabulum of FIG. 1 with one bone screw.

Referring to FIG. 1, the artificial acetabulum includes an outer metal shell 1, for example, of titanium, which is provided in the region of low "geographic" latitudes with outer threads 2 for threading into a pelvic bone (not shown) In addition, a threaded bore 3 is disposed on a central axis 4 which defines a polar axis as well as an axis of symmetry for the shell. The threaded bore 3 is sized so as to receive a setting and screwing-in instrument (not shown) in order to be threaded into a pelvic bone while being kept centered. The shell 1 also has a plurality of annular grooves 5 (see FIG. 1) in the vicinity of the pole which serve for tissue to grow into and adhere.

Referring to FIGS. 1 and 2, the metal shell also includes two circumferential rows of bores 6. At least some of the bores provide for the passage of a bone screw 7. In this respect, as indicated in FIG. 1, each bore which receives a bone screw 7 may be enlarged on the inside in such a way that the head (not shown) of a screw 7 can be sunk into the outer shell 1.

The metal shell 1 also has an annular shoulder in the form of a stepped-shape offset 8 about the equatorial edge. In addition, a wall of the offset 8 is provided with threads 9 and in order to avoid a sharp edge at the transition of the offset 8 into the interior hollow space of the shell 1, a chamfer surface 10 is provided therebetween.

The acetabulum also includes a one-piece synthetic acetabular body 11 which is initially rotatably mounted in the outer shell 1. This body 11 includes an acetabular shell 12 having a socket for receiving a spherical joint head (not shown). In addition, the acetabular body 11 has an extension 14 which extends from the metal shell 1 in asymmetric relation about the polar axis 4 as well an annular flange 15. The extension 14 as indicated in FIG. 1, points laterally and serves to prevent dislocations of the joint head from the socket upon extreme deflections of a hip joint. The annular flange 15 is seated on the shoulder 8 of the shell 1 and is able to rotate about the polar axis 4 while sliding on the shoulder 8.

The acetabulum also includes a ring 16 which is mounted in the metal shell 1 in secured relation in order to clamp the flange 15 against the shoulder 8. In this respect, the ring 16 is a threaded ring which can be screwed into the threads 9 of the shell 1 and brought against the flange 15 of the acetabular body 11 to secure the body 11 against rotation relative to the shell 1. In addition, the ring 16 may be made of the same material as the outer shell 1.

Referring to FIG. 1, the acetabular body 11 is provided with a plurality of bores 17 (only one of which is shown) which are distributed circumferentially for engagement with a setting instrument.

Implantation of the acetabulum may take place, for example, in that the outer shell 1 is initially screwed into a prepared pelvic bone via a screwing-in instrument centered in the bore 3 and engaging at least some of the bores 6. Subsequently, the outer shell 1, if necessary, is further anchored with bone screws 7.

Next, the acetabular body 11 is set into the outer shell 1 by means of a setting instrument which engages within the bores 17. In this respect, the acetabular body 11 is fitted into the shell 1 so that the flange 15 rests on the shoulder 8 and is rotated into the proper position for the extension 14.

Thereafter, the threaded ring 16 is threaded into the shell 1 and tightened so far with a screwing-in instrument until the degree of clamping required for a secure and nondisplacable fit of the body 11 in the shell 1 has been achieved In this respect, the screwing-in instrument, for example a screw cap, for the ring 16 may be expediently combined with the setting instrument for the acetaular body 11.

In order to be rotated, the threaded ring 16 receives a screwing-in instrument which may engage fewer recesses (not shown) distributed regularly on the outer face of the ring 16.

The invention thus provides an acetabulum wherein the acetabular body can be precisely positioned within the metal shell relative to a polar axis of the shell and secured in that position.

The invention further provides for a precise setting of an acetabular body which is shaped in an asymmetric manner with respect to the polar axis on a particular meridian of the shell, for example, relative to the frontal plane of the human body.

What is claimed is:

1. An artificial acetabulum comprising
an outer metal shell having a cavity and an annular shoulder about said cavity;
a one piece synthetic acetabular body mounted in said cavity of said metal shell, said body including a socket for receiving a spherical joint head and an annular flange seated on said shoulder of said shell; and
a ring mounted in said metal shell and against said flange to clamp said flange against said shoulder to prevent displacement of said body in said shell.

2. An artificial acetabulum as set forth in claim 1 wherein said body has an extension extending from said shell in asymmetric relation for preventing dislocations of the joint head from said socket upon extreme deflections of a hip joint.

3. An artificial acetabulum as set forth in claim 2 wherein said shell has at least two circumferential rows of bores.

4. An artificial acetabulum as set forth in claim 1 wherein said ring is threaded into said shell.

5. An artificial acetabulum comprising
a metal shell having an annular shoulder and a threaded bore disposed on a central axis;
a synthetic acetabular body mounted in said shell, said body including a socket for receiving a spherical joint head, an annular flange seated on said shoulder and an extension extending from said shell in asymmetric relation to said shell axis; and
a ring threaded into said shell to clamp said flange against said shoulder.

6. An artificial acetabulum comprising
an outer metal shell having a hemispherical cavity and an annular shoulder about said cavity;
a synthetic acetabular body rotatably mounted in said cavity of said metal shell, said body including a socket for receiving a spherical joint head and an annular flange seated on said shoulder of said shell; and
a ring mounted in said metal shell and against said flange to clamp said flange against said shoulder to secure said body against rotation relative to said shell.

7. An artificial acetabulum as set forth in claim 6 wherein said body has an extension extending from said shell in asymmetric relation for preventing dislocations of the joint head from said socket upon extreme deflections of a hip joint.

8. An artificial acetabulum as set forth in claim 6 wherein said ring is threaded into said shell.

* * * * *

UNITED STATES PATENT AND TRADEMARK OFFICE
CERTIFICATE OF CORRECTION

PATENT NO. : 4,871,368

DATED : October 3, 1989

INVENTOR(S) : HEINZ Wagner

It is certified that error appears in the above-identified patent and that said Letters Patent is hereby corrected as shown below:

```
Column 1, line 14 "shell In" should be -shell.  In-
Column 1, line 16 "shell" should be -shell.-
Column 3, line 21 "fewer" should be -four-
```

Signed and Sealed this

Eighteenth Day of December, 1990

Attest:

HARRY F. MANBECK, JR.

*Attesting Officer*      *Commissioner of Patents and Trademarks*